Ｕnited States Patent (12) United States Patent
Wang et al.

(10) Patent No.: US 12,146,881 B2
(45) Date of Patent: Nov. 19, 2024

(54) REAGENT COMPOSITION FOR DETECTION OF NON-HEMATOPOIETIC TUMOR AND USE THEREOF

(71) Applicants: Synarc Research Laboratory (Beijing) Ltd., Beijing (CN); HEBEI YANDA LUDAOPEI HOSPITAL, Langfang (CN)

(72) Inventors: Hui Wang, Beijing (CN); Man Chen, Beijing (CN); Aixian Wang, Beijing (CN); Meiwei Gong, Beijing (CN); Xueying Wu, Beijing (CN); Junyi Zhen, Beijing (CN); Qing Du, Beijing (CN); Ya Guo, Beijing (CN)

(73) Assignees: Synarc Research Laboratory (Beijing) Ltd., Beijing (CN); HEBEI YANDA LUDAOPEI HOSPITAL, Langfang (CN)

( * ) Notice: Subject to any disclaimer, the term of this patent is extended or adjusted under 35 U.S.C. 154(b) by 0 days.

(21) Appl. No.: 18/209,814

(22) Filed: Jun. 14, 2023

(65) Prior Publication Data

US 2023/0408524 A1    Dec. 21, 2023

(30) Foreign Application Priority Data

Jun. 17, 2022 (CN) .......................... 202210686077.3

(51) Int. Cl.
*G01N 33/574* (2006.01)

(52) U.S. Cl.
CPC .................. *G01N 33/57492* (2013.01); *G01N 2333/70503* (2013.01); *G01N 2333/7051* (2013.01); *G01N 2333/70514* (2013.01); *G01N 2333/70589* (2013.01); *G01N 2333/70596* (2013.01)

(58) Field of Classification Search
CPC ... G01N 33/57492; G01N 2333/70503; G01N 2333/7051; G01N 2333/70514; G01N 2333/70589; G01N 2333/70596
See application file for complete search history.

(56) References Cited

U.S. PATENT DOCUMENTS

| 5,877,299 A | 3/1999 | Thomas et al. |
| 6,117,985 A | 9/2000 | Thomas et al. |
| 2016/0264652 A1* | 9/2016 | Durrant .................. C07K 16/18 |

FOREIGN PATENT DOCUMENTS

| CN | 101516912 A | 8/2009 |
| CN | 101624579 A | 1/2010 |
| CN | 107753954 A | 3/2018 |
| CN | 108290939 A | 7/2018 |
| CN | 112462065 A | 3/2021 |
| CN | 113933513 A | 1/2022 |

OTHER PUBLICATIONS

Ferreira-Facio et al. Flow Cytometry Immunophenotyping for Diagnostic Orientation and Classification of Pediatric Cancer Based on the EuroFlow Solid Tumor Orientation Tube (STOT). Cancers 13 (4945): 1-27 (Sep. 30, 2021).*
Enciu et al. Targeting CD36 as Biomarker for Metastasis Prognostic: How Far from Translation into Clinical Practice? BioMed Research International vol. 2018, Article ID 7801202 (Jul. 4, 2018).*
Becton Dickinson .Design of Multicolor Flow Cytometry Panels Incorporating BD Horizon Brilliant Violet Dyes (2013)).*
Cho et al. Novel and Emerging Surveillance Markers for Bladder Cancer. Bladder Cancer (2018): Abstract.*
Fromm et al., Characterization and Purification of Neoplastic Cells of Nodular Lymphocyte Predominant Hodgkin Lymphoma from Lymph Nodes by Flow Cytometric Cell Sorting, the American Journal of Pathology, vol. 187, No. 2, Feb. 2017, 14 pages.
Search Report for CN Application No. 202210686077.3, dated Jul. 25, 2022, 7 pages, Translation.
Shen et al., An anti-transferrin receptor antibody enhanced the growth inhibitory effects of chemotherapeutic drugs on human non-hematopoietic tumor cells, International Immunopharmacology, vol. 8, No. 13-14, 1813-1820, 2008, 8 pages.
Wang et al., Detection of bone marrow involved by nonhematopoietic neoplasms using flow cytometry, China J Lab Med, vol. 34, No. 2, Feb. 2011, 6 pages.

* cited by examiner

*Primary Examiner* — Gailene Gabel
(74) *Attorney, Agent, or Firm* — FOLEY & LARDNER LLP (57) ABSTRACT

The present invention provides a reagent composition for detection of a non-hematopoietic tumor and use thereof. Said reagent composition includes three sets of antibodies, with the first set of antibodies including an anti-CD9 antibody, an anti-GD2 antibody, an anti-CD3 antibody, an anti-CD4 antibody, an anti-CD56 antibody, an anti-CD36 antibody, an anti-CD81, and an anti-CD45 antibody; the second set of antibodies including an anti-HLA-ABC antibody, an anti-CD38 antibody, an anti-CD19 antibody, an anti-CD56 antibody, an anti-CD36 antibody, an anti-CD7 antibody, and an anti-CD45 antibody; the third set of antibodies including anti-cytoplasmic cytokeratin antibodies; wherein the first set of antibodies and the second set of antibodies are respectively used for samples in separate tubes, and the third set of antibodies is used for the sample in the same tube as the second set of antibodies. The reagent composition of the present invention can be applied for flow cytometry screening, diagnosis and/or follow-up detection of a non-hematopoietic tumor.

4 Claims, 6 Drawing Sheets

REAGENT COMPOSITION FOR DETECTION OF NON-HEMATOPOIETIC TUMOR AND USE THEREOF

CROSS-REFERENCE TO RELATED APPLICATION

This application claims the benefit of and priority to Chinese Patent Application No. 202210686077.3, filed Jun. 17, 2022, which is incorporated by reference herein in its entirety.

TECHNICAL FIELD

The present invention relates to a reagent composition for detection of a non-hematopoietic tumor and use thereof where the detection includes screening, diagnosis and/or follow-up detection, which pertains to the field of biomedical technology.

BACKGROUND

Malignant tumors have always been a major disorder affecting human health. Early screening, diagnosis and treatment of tumors can greatly improve the complete remission rate and survival rate. The techniques for diagnosing and following-up of lymphohematopoietic tumors have been developed for many years and are relatively mature, and made great achievements especially due to the rise of targeted therapies in recent years. As for non-hematopoietic tumors, such as malignant epithelial-derived tumors (e.g., lung cancer, breast cancer, gallbladder cancer, colon cancer, prostate cancer, esophageal cancer, fallopian tube cancer, head and neck cancer, hepatoblastoma, pancreatoblastoma, pancreatic cancer, etc.), embryonal tumors (neuroblastoma, retinoblastoma, germ cell tumor, medulloblastoma, primitive neuroectodermal tumor (PNET), etc.), soft tissue tumors and extraosseous sarcomas (Ewing sarcoma or rhabdomyosarcoma), bone tumors and cartilage tumors (osteosarcoma or soft tissue sarcoma), malignant renal tumors (nephroblastoma, adrenal carcinoma, or renal clear cell carcinoma), malignant melanoma and the like, the diagnosis has been mainly relying on imaging and pathology from fine needle aspiration or biopsy for a long time. However, imaging is not sensitive enough, surgery is an invasive technique, and some masses are inconvenient to remove, while sometimes more accessory techniques are necessary to make a clear diagnosis. In addition, after surgical resection, no more material is available for following up. Therefore, there is an urgent need for a highly sensitive and relatively non-invasive technique to assist the screening and/or diagnosis and follow-up of non-hematopoietic tumors.

Flow cytometry is a technique that employs antigen-antibody binding and laser-excited fluorescence to detect cell surface and intracytoplasmic immunological markers for identifying cells with high sensitivity and specificity, and plays an essential role in the diagnosis and follow-up of lymphohematopoietic tumors. However, the use of flow cytometry in the diagnosis of non-hematopoietic tumors has been rarely reported mainly because, due to the wide variety of non-hematopoietic tumors, the limitations of sampling and techniques, and the lack of profound understanding of non-hematopoietic tumor markers in the art, it is difficult to establish a relatively fixed, extensive and standardized assaying protocol, and therefore it has not been widely used for a long time.

In order to solve this problem, explorative investigations have been conducted by researchers, including the protocols continuously launched by the EuroFlow Consortium (EuroFlow) starting from 2012, and an article published in 2021 on the protocol of detecting non-hematopoietic tumors in children. Nonetheless, the EuroFlow protocols still have the following drawbacks: 1) mainly regarding the conception of the identification of hematopoietic tumors, the exclusion is not comprehensive enough, and missed diagnosis of $CD56^-$ metastasis tends to occur; 2) there lacks markers with high coverage in the protocols, and even though the markers GD2, EpCAM, and numyogenin/nuMyoD1 used therein are relatively specific, in fact GD2 only covers neuroblastoma and some types of melanoma, and EpCAM is only seen in tumors of epithelial origin and is not a marker with high coverage, while numyogenin/nuMyoD1 only covers rhabdomyosarcoma; 3) the protocols have inadequate differentiation of hematopoietic tumors, probably because it targets tumors in children: in the diagnosis of non-hematopoietic tumors, it is important to differentiate $CD45^-/CD56^+$ and $CD45^-/CD56^-$ lymphohematopoietic tumors, but in these protocol CD271, CD9, CD90, and CD99 markers are used, which markers are also highly expressed in the lymphohematopoietic cells, have a rather low coverage in the non-hematopoietic tumor, and therefore have insufficient potency of distinction; further, in terms of the differential diagnosis with hematopoietic tumors, cytoplasmic CD3, CD3, CD4, CD8, CD19 are used, which can only cover B-cell tumors, T-cell tumors, and blastic plasmacytoid dendritic cell neoplasm, but not plasma cell tumors, NK tumors, acute megakaryocytic leukemia, and acute erythroleukemia, and therefore $CD45^-/CD56^+$ and $CD45^-/CD56^-$ lymphohematopoietic tumors cannot be completely excluded.

Upon search, there is no solution in the prior art that is useful for screening/diagnosis and follow-up of non-hematopoietic tumors by flow cytometry, and is applicable to all populations including adults and children, while having high coverage and good specificity, with relevant fixed standards.

SUMMARY OF THE INVENTION

An object of the present invention is to provide a reagent composition suitable for detection of a non-hematopoietic tumor by highly sensitive, specific, and universal flow cytometry with or without any clinical information.

A further object of the present invention is to provide use of the reagent composition in the detection of non-hematopoietic tumor.

In the present invention, the detection includes screening, diagnostic and/or follow-up detection.

The term "non-hematopoietic tumor" in the present invention refers to most types of solid tumors other than lymphohematopoietic tumors as published by the World Health Organization, including: malignant tumors of epithelial origin (e.g., lung cancer, breast cancer, gallbladder cancer, colon cancer, prostate cancer, esophageal cancer, fallopian tube cancer, head and neck cancer, hepatoblastoma, pancreaticoblastoma, pancreatic cancer, etc.), embryonal tumors (neuroblastoma, retinoblastoma, germ cell tumor, medulloblastoma, primitive neuroectodermal tumor (PNET), etc.), soft tissue tumors and extraosseous sarcomas (Ewing sarcoma, rhabdomyosarcoma, etc.), bone tumors and cartilage tumors (osteosarcoma, soft tissue sarcoma, etc.), malignant kidney tumors (nephroblastoma, adrenal carcinoma, renal clear cell carcinoma, etc.), malignant melanoma, etc.

In one aspect, the present invention provides a reagent composition that can be used for detection of a non-hematopoietic tumor by flow cytometry, wherein the reagent composition includes a first set of antibodies, a second set of antibodies, and a third set of antibodies, wherein, the first set of antibodies includes: an anti-CD9 antibody, an anti-GD2 antibody, an anti-CD3 antibody, an anti-CD4 antibody, an anti-CD56 antibody, an anti-CD36 antibody, an anti-CD81 antibody, and an anti-CD45 antibody; and the first set of antibodies is to be added to a first flow cytometric tube in which a sample to be assayed is in the form of a single cell suspension, the second set of antibodies includes: an anti-HLA-ABC antibody, an anti-CD38 antibody, an anti-CD19 antibody, an anti-CD56 antibody, an anti-CD36 antibody, an anti-CD7 antibody, and an anti-CD45 antibody; and the second set of antibodies is to be added to a second flow cytometric tube in which a sample to be assayed is in the form of a single cell suspension, the third set of antibodies includes: anti-cytoplasmic cytokeratin (CK) antibodies; and the third set of antibodies is to be added to the second flow cytometric tube to which the second set of antibodies has been added and permeabilization has been performed.

The reagent composition of the present invention can be applied to flow cytometry screening and/or diagnosis and follow-up of non-hematopoietic tumors, including: tumors of malignant epithelial origin (e.g., lung cancer, breast cancer, gallbladder cancer, colon cancer, prostate cancer, esophageal cancer, fallopian tube cancer, head and neck cancer, hepatoblastoma, pancreatoblastoma, pancreatic cancer, etc.), embryonal tumors (neuroblastoma, retinoblastoma, germ cell tumor, medulloblastoma, primitive neuroectodermal tumor (PNET), etc.), soft tissue tumors and extraosseous sarcomas (Ewing sarcoma, rhabdomyosarcoma, etc.), bone tumors and cartilage tumors (osteosarcoma, soft tissue sarcoma, etc.), malignant kidney tumors (nephroblastoma, adrenal carcinoma, renal clear cell carcinoma, etc.), malignant melanoma, etc. Both highly sensitive and specific diagnosis and follow-ups after treatment to form standardized protocols are enabled, thereby improving efficiency and accuracy, and facilitating automation and artificial intelligence in the future.

According to a specific embodiment of the present invention, each antibody in the antibody composition of the present invention is a monoclonal antibody, wherein the anti-cytoplasmic cytokeratin (CK) antibody is a complex comprising an anti-CK8 monoclonal antibody, an anti-CK18 monoclonal antibody to CK18, and an anti-CK19 monoclonal antibody.

According to a specific embodiment of the present invention, each antibody in the antibody composition of the present invention is a fluorescein-labeled antibody. Preferably, in the first set of antibodies, the anti-CD9 antibody, the anti-GD2 antibody, the anti-CD3 antibody, the anti-CD4 antibody, the anti-CD56 antibody, the anti-CD36 antibody, the anti-CD81 antibody, and the anti-CD45 antibody are fluorescein-labeled with FITC, PE, PerCP-Cy5.5, PE-Cy7, APC, APC-Cy7, BV421, and V500, respectively. In the second set of antibodies, the anti-HLA-ABC antibody, the anti-CD38 antibody, the anti-CD19 antibody, the anti-CD56 antibody, the anti-CD36 antibody, the anti-CD7 antibody, and the anti-CD45 antibody are fluorescein-labeled with PE, PerCP-Cy5.5, PE-Cy7, APC, APC-Cy7, BV421, and V500, respectively. In the third set of antibodies, the anti-cytoplasmic cytokeratin (CK) antibody is fluorescein-labeled with FITC. By pairing different antibodies with specific fluorescein in the present invention, it is possible to achieve excellent staining of all fluoresceins in each channel when the antibody composition of the present invention is applied for screening and/or diagnosis and follow-up of non-hematopoietic tumors.

According to specific embodiments of the present invention, each antibody component in the antibody composition of the present invention is commercially available. Each antibody should meet the requirements of relevant industry standards. Among them, the anti-cytoplasmic cytokeratin (CK) antibody with the clone number CK3-6H5 can be used as the anti-cytoplasmic cytokeratin (CK) antibody.

According to a specific embodiment of the present invention, in the antibody composition of the present invention, the first set of antibodies is a mixture of an anti-CD9 antibody, an anti-GD2 antibody, an anti-CD3 antibody, an anti-CD4 antibody, an anti-CD56 antibody, an anti-CD36 antibody, an anti-CD81 antibody, and an anti-CD45 antibody mixed in a volume ratio of 5:5:5:3:2:3:3:3, and the second set of antibodies is a mixture of an anti-HLA-ABC antibody, an anti-CD38 antibody, an anti-CD19 antibody, an anti-CD56 antibody, an anti-CD36 antibody, an anti-CD7 antibody, and an anti-CD45 antibody mixed in a volume ratio of 5:5:3:2:3:3:3. All the above-mentioned mixing ratios of various antibodies refer to the mixing ratio where each of the antibodies has a substantially equivalent potency.

Another aspect of the present invention provides a kit comprising a plurality of containers, each container separately containing each set of antibodies (the first set of antibodies, the second set of antibodies, the third set of antibodies) of the reagent composition described herein.

According to specific embodiments of the present invention, the kit of the present invention may also include one or more of: hemolysin, a permeabilization reagent, a buffer, and flow cytometric tubes for use with a flow cytometer. These reagents and consumables are commercially available. The permeabilization reagent is preferably a permeabilization reagent comprising a solution A and a solution B. Each reagent material may be accommodated in separate containers.

The kit of the present invention can be used for screening, diagnosis and/or follow-up detection of non-hematopoietic tumors. The non-hematopoietic tumors correspond to the vast majority of types of solid tumors other than lymphohematopoietic tumors, as published by the World Health Organization, and include: malignant tumor of epithelial origin, embryonal tumor, soft tissue tumor, extraosseous sarcoma, hard bone tumor, cartilage tumor, malignant kidney tumor, and malignant melanoma.

Another aspect of the present invention also provides use of the antibody composition in the preparation of flow cytometry loading samples for detection of a non-hematopoietic tumor.

According to a specific embodiment of the present invention, a process for the preparation of a flow cytometry loading sample for detection of a non-hematopoietic tumor includes the steps of (1) adding samples to be assayed into two flow cytometric tubes, a first tube and a second tube, respectively, to form a single cell suspension and ensure a cell amount of $1 \times 10^6$/tube to $1 \times 10^7$/tube, (2) adding to the first tube obtained from the treatment in step (1) the first set of antibodies in the reagent composition according to the invention, adding to the second tube obtained from the treatment in step (1) the second set of antibodies in the reagent composition according to the invention, and incubating at room temperature in dark, (3) adding a solution of a permeabilization reagent A to the second tube after the incubation in step (2), and continuing the incubation at room temperature in dark, (4) adding 1× hemolysin to the first flow cytometric tube after the incubation in step (2) and adding 1× hemolysin to the second flow cytometric tube after the incubation in step (3), and continuing the incubation at room temperature in dark, (5) centrifuging each flow cytometric tube after the incubation in step (4) and removing the supernatant, (6) adding to the second tube after removing the supernatant in step (5) a solution of a permeabilization reagent B and the third set of antibodies of the reagent composition according to the invention, and incubating at room temperature in dark, and (7) adding a PBS buffer for washing to the first tube after removing the supernatant in step (5) and to the second tube after the incubation in step (6), respectively, followed by centrifugation, removal of supernatant, and resuspension of cells with a PBS buffer, to obtain a sample for flow cytometry detection.

In the present invention, when steps of operation are described, the order in the description of the operational steps is not intended to limit the order in which these steps are actually operated, unless specifically stated or a sequential relationship can be clearly established in the context.

According to a specific embodiment of the present invention, the sample to be assayed in the present invention may be bone marrow or peripheral blood, but may also be any samples that can be prepared as single live cells and are suitable for flow cytometry assay, such as a tissue sample, a body fluid sample and the like.

According to a specific embodiment of the present invention, in step (1), the volume of the sample added per tube does not exceed 160 μL (when the count of peripheral blood cells from the patient is low, a volume more than 160 μL can be added first as needed, followed by concentration by centrifugation and removing the supernatant).

According to a specific embodiment of the invention, each reagent can be used in an amount with reference to the conventional amount in the prior art in the field or according to the amount recommended by the manufacturer.

According to a specific embodiment of the present invention, for the reagent composition of the present invention, the addition amount of the first set of antibodies is 15-58 μL/tube, the addition amount of the second set of antibodies is 12-48 μL/tube, and the addition amount of the third set of antibodies is 3-10 μL/tube.

According to a specific embodiment of the present invention, the amount of each addition of PBS is 2-3 mL/tube, and the centrifugation condition may be 1,000 to 2,000 rpm (or 300 to 450 g) for 5 minutes.

According to a specific embodiment of the present invention, the incubation duration in step (2) may be 10-30 minutes.

According to a specific embodiment of the present invention, the incubation duration in step (3) may be 5-20 minutes. The solution A of the permeabilization reagent can be added in an amount recommended by the manufacturer, usually 100 μL/tube.

According to a specific embodiment of the present invention, the incubation duration in step (4) may be 5-30 minutes. 1× hemolysin is added in an amount of 2-3 mL/tube.

According to a specific embodiment of the present invention, in step (6), an incubation for about 10-30 minutes is usually needed. The centrifugation condition may be 1,000 to 2,000 rpm (or 300 to 450 g) for 5 minutes.

According to a specific embodiment of the present invention, in step (6), the solution B of the permeabilization reagent can be added in an amount recommended by the manufacturer, usually 50 μL/tube.

According to a specific embodiment of the present invention, in step (7), the PBS buffer for washing is added in an amount of 2-3 mL/tube. The centrifugation conditions may be 1,000 to 2,000 rpm (or 300 to 450 g) for 5 minutes. The PBS buffer for resuspension is added in an amount of 0.5-1 mL/tube.

According to a specific embodiment of the present invention, when the resuspended cells are subjected to flow cytometry, for the first tube sample, a gate is set by the combination of CD45 and SSC, and gates are set by the combination of CD56, GD2, and CD36, respectively, together with CD45; for the second tube sample, a gated is set with the combination of CD45 and SSC, and gates are set by the combination of CD56, cytokeratin, and CD36, respectively, together with CD45; CD45$^-$/CD56$^+$ or CD45$^-$/GD2$^+$ or CD45$^-$/cytokeratin$^+$ or CD45$^-$/CD56$^-$/GD2$^-$/cytokeratin$^-$/CD36$^-$ and/or HLA-ABC$^-$ cells are screened (plasma cell tumors, acute B-lymphoblastic leukemia, acute megakaryocytic leukemia, and in a few rare cases, other CD45-negative lymphohematopoietic tumors should be exclude, and omission of CD45$^-$/CD56$^-$/GD2$^-$/cytokeratin$^-$ non-hematopoietic tumors should be avoided), and analysis are then performed.

In another aspect, the present invention also provides a device for detection of a non-hematopoietic tumor, wherein the detection includes screening, diagnosis and/or follow-up detection, and the device comprises a detection unit and an analysis unit, and wherein, said detection unit comprises reagent materials for assaying by flow cytometry a sample from a subject, to obtain detection results of the sample; said reagent materials comprise the reagent composition according to the invention, and said analysis unit is used to analyze the detection results from the detection unit.

According to a specific embodiment of the present invention, in the device for detection of a non-hematopoietic tumor of the present invention, the process of application of the detection unit includes: preparing a flow cytometry loading sample after processing the sample to be assayed with the antibody composition according to the present invention; and performing a flow cytometry assay. The process of analysis of the analysis unit includes: analyzing the assay results to discriminate (including auxiliary discrimination of) non-hematopoietic tumors, i.e., the vast majority of types of solid tumors other than lymphohematopoietic tumors as published by the World Health Organization, including: tumors of malignant epithelial origin (e.g., lung cancer, breast cancer, gallbladder cancer, colon cancer, prostate cancer, esophageal cancer, fallopian tube cancer, head and neck cancer, liver blastoma, pancreaticoblastoma, pancreatic cancer, etc.), embryonal tumors (neuroblastoma, retinoblastoma, germ cell tumor, medulloblastoma, primitive neuroectodermal tumor (PNET), etc.), soft tissue tumors and extraosseous sarcomas (Ewing sarcoma, rhabdomyosarcoma, etc.), bone tumors and cartilage tumors (osteosarcoma, soft tissue sarcoma, etc.), malignant renal tumors (nephroblastoma, adrenal carcinoma, renal clear cell carcinoma, etc.), malignant melanoma and the like.

According to a specific embodiment of the present invention, when the device of the present invention is used for detection of a non-hematopoietic tumor, the process of assaying by flow cytometry a sample from a subject comprises:
preparing a flow cytometry loading sample after treating the sample to be assayed with the reagent composition according to the invention, and
performing a flow cytometry assay.

According to a specific embodiment of the present invention, when the device of the present invention is used for detection of a non-hematopoietic tumor, the gating and analysis for each flow cytometric tube may be carried out according to the following procedure:
in the flow cytometry assay, the gates for the first tube are set as follows: an adherent cell removal gate P1 is set, and a live cell gate P2 is set within P1 to obtain single live cells; blood cells are each gated within the gate P2 with CD45/SSC antibodies; within the gate P2, a gate NH1 is set with CD45/CD56 antibodies to detect CD45$^-$/CD56$^+$ cells, and a gate NH2 is set with CD45/GD2 antibodies to detect CD45$^-$/GD2$^+$ cells; the expression of CD3/CD4/CD36/CD9/CD81 cells in the gates NH1 and NH2 is shown; preferably, furthermore, within the gate P2, a gate NH3 is set with CD45/CD36 antibodies to detect CD45$^-$/CD36$^-$ cells; and the expression of CD9/GD2/CD56/CD81 in the cells within the gate NH3 is shown; and
in the flow cytometry assay, the gates for the second tube are set as follows: an adherent cell removal gate P1 is set, and a live cell gate P2 is set within P1 to obtain single live cells; blood cells are each gated within the gate P2 with CD45/SSC antibodies; within the gate P2, a gate NH4 is set with CD45/CD56 antibodies to detect CD45$^-$/CD56$^+$ cells, a gate NH5 is set with CD45/cytoplasmic cytokeratin antibodies to detect CD45$^-$/cytokeratin$^+$ cells; the expressions of HLA-ABC/CD38/CD19/CD36/CD7 cells in the gates NH4 and NH5 are displayed; preferably, furthermore, within the gate P2, a gate NH6 is set with CD45/CD36 antibodies to detect CD45$^-$/CD36$^-$ cells; and the expressions of cytokeratin/HLA-ABC/CD38/CD56 in the cells within the gate NH6 are displayed.

In some specific embodiments of the present invention, when the device of the present invention is used for the detection of non-hematopoietic tumors, in the flow cytometry assay, the gates for the first tube are set as follows: an adherent cell removal gate P1 is set with FSC-A/H, and a live cell gate P2 is set within the gate P1 with FSC/SSC to obtain single live cells; blood cells (including eosinophils) are each gated within the gate P2 with CD45/SSC antibodies; within the gate P2, a gate NH1 is set with CD45/CD56 antibodies to detect CD45$^-$/CD56$^+$ cells, which can screen out the vast majority of non-hematopoietic tumors (with over 90% as reported in the literature, and 96.65% based on statistics according to the present invention), and a gate NH2 is set with CD45/GD2 antibodies to detect CD45$^-$/GD2$^+$ cells that are mainly found in neuroblastoma and most types of melanomas and also expressed to a varying extent in other bone and soft tissue tumors, small cell lung cancer, and brain tumors; within the gate P2, a gate NH3 is set with CD45/CD36 to determine the presence or absence of CD45$^-$/CD36$^-$ cells. The expressions of CD3/CD4/CD36/CD9/CD81 in the cells within the gates NH1 and NH2 are displayed, CD3$^+$ T cells, CD4$^+$ T cells, CD4dim monocytes or blastic plasmacytoid dendritic cells, and CD36$^+$ nucleated red blood cells, megakaryocytes and monocytes are excluded, and CD81 and/or CD9 are expressed in the vast majority of non-hematopoietic tumors such as neuroblastoma; The expressions of CD9/GD2/CD56/CD81 in the cells within the gate NH3 are displayed, and caution is to be taken not to miss CD45$^-$/GD2$^-$/CD56$^-$/CD36$^-$ cells of non-hematopoietic tumors, most of which express CD81$^+$ and/or CD9$^+$.

In some specific embodiments of the present invention, when the device of the present invention is used for the detection of non-hematopoietic tumors, in the flow cytometry assay, the gates for the second tube are set as follows: an adherent cell removal gate P1 is set with FSC-A/H, and a live cell gate P2 is set within the gate P1 with CD45/SSC to obtain single live cells; blood cells are each gated within the gate P2 with CD45/SSC antibodies; within the gate P2, a gate NH4 is set with CD45/CD56 antibodies to detect CD45$^-$/CD56$^+$ cells, which can screen out the vast majority of non-hematopoietic tumors; a gate NH5 is set with CD45/cytoplasmic cytokeratin antibodies to detect CD45$^-$/cytokeratin$^+$ cells mainly found in tumor cells of epithelial origin (based on the investigation of cell lines and clinical sample assaying according to the present invention, there is a CD45$^-$/cytokeratin$^+$ positivity rate of 94.59% in tumor cells of epithelial origin); within the gate P2, a NH6 gate is set with CD45/CD36 to determine the presence or absence of CD45$^-$/CD36$^-$ cells. The expressions of HLA-ABC/CD38/CD19/CD36/CD7 in the cells within the gates NH4 and NH5 are displayed, CD38 positive benign and malignant plasma cells, various acute leukemia cells and the like, CD19$^+$ B cells and/or plasma cells, CD36$^+$ nucleated erythrocytes, megakaryocytes and monocytes, CD7$^+$ T cells, NK cells and other dendritic cell tumors and acute myeloid leukemia with abnormal expression of CD7 are excluded, nearly all of which express HLA-ABC, statistically 99% or more according to the invention. The expressions of cytokeratin/HLA-ABC/CD38/CD56 in the cells within the gate NH6 are displayed, and caution is to be taken not to miss CD45$^-$/cytokeratin$^-$/CD56$^-$/CD36$^-$ cells of non-hematopoietic tumors, most of which are present in CD38$^-$/HLA-ABC$^-$ (with a 95.40% of CD38$^-$ and 93.10% of HLA-ABC$^-$, as shown by experimental statistics of the present invention) non-hematopoietic tumors.

According to a specific embodiment of the present invention, in the device for the detection of non-hematopoietic tumors of the present invention, the analysis unit may further comprise a module for further identification of diseases based on the results of gated analysis assay (the identification according to the present invention includes screening, suggestion, auxiliary diagnosis, diagnosis, and follow-up of minimal residual diseases). In the present invention, by comparing the cell populations displayed within the gates set up by a multi-marker combination with corresponding normal cells, tumor cells are identified, lymphohematopoietic tumors and non-specific staining are excluded, the nature of non-hematopoietic tumors are determined, and differentiation of common subtypes is carried out.

Specifically, the present invention can be used to screen and/or diagnose and follow up, in a highly sensitive, specific and comprehensive manner, virtually all non-hematopoietic tumors. Here, non-hematopoietic tumors in the context refer to the vast majority of types of corresponding solid tumors other than lymphohematopoietic tumors as published by the World Health Organization, including: tumors of malignant epithelial origin (e.g., lung cancer, breast cancer, gallbladder cancer, colon cancer, prostate cancer, esophageal cancer, fallopian tube cancer, head and neck cancer, hepatoblastoma, pancreatoblastoma, pancreatic cancer, etc.), embryonal tumors (neuroblastoma, retinoblastoma germ cell tumor, medulloblastoma, primitive neuroectodermal tumor (PNET), etc.), soft tissue tumors and extraosseous sarcomas (Ewing sarcoma, rhabdomyosarcoma, etc.), bone tumors and cartilage tumors (osteosarcoma, soft tissue sarcoma, etc.), malignant kidney tumors (nephroblastoma, adrenal carcinoma, renal clear cell carcinoma, etc.), malignant melanoma and the like.

According to a specific embodiment of the present invention, in the analysis of samples in two tubes of in the present invention, CD45/SSC is universally used in both tubes for preliminary screening of various populations of cells (mature lymphocytes, monocytes, differentiated stage granulocytes, nucleated red blood cells) commonly found in normal samples to determine whether they are in a normal proportion and the presence or absence of a high proportion of tumor cells, and further determination is made in combination with other markers in each tube. Specifically, determination of each type of disease may be made as follows.

(1) Identification of tumor cells: a CD45/SSC gating plot of normal samples of each tube is mainly composed of lymphocyte gates (lym), monocyte gates (mono), granulocyte gates (gra), and nucleated red blood cell gates (NRBC), surrounding small areas of CD45dim/SSC (primitive cell pores) in a question mark-like shape. $CD45^-/CD56^+$ and/or $GD2^+$, $CD45^-/CD56^+$ and/or cytokeratin$^+$, and $CD45^-/CD56^-/GD2^-/$cytokeratin$^-/CD36^-/HLA\text{-}ABC^-$ cells are not present in normal bone marrow. At this time, the following determination is further made according to the circumstances:

1) Exclusion of lymphohematopoietic tumors: in the identification (differentiation) of lymphohematopoietic tumors from non-hematopoietic tumors, GD2 and cytokeratin have a specificity of almost 99% or higher, and therefore mainly in the case of GD2 and cytokeratin both being negative, $CD45^-/CD56^+$ or $CD45^-/CD56^-$ lymphohematopoietic tumors are then identified, which are mostly found in acute B-lymphoblastic leukemia and plasma cell tumors, and less often in acute megakaryocytic leukemia, acute erythroleukemia, blastic plasmacytoid dendritic cell neoplasm, and other lymphohematopoietic tumors. 98% of acute B-lymphoblastic leukemia expresses CD19, with 90% or more expressing CD38, and almost 100% expressing HLA-ABC; 100% of plasma cell tumors express CD38, with 95% expressing HLA-ABC; with an extremely low morbidity, almost 100% of acute megakaryocytic leukemia expresses HLA-ABC, with 90% or more expressing CD38, 80% or more expressing CD36, and 60% expressing CD4; acute erythroleukemia has a very low incidence, and 95% or more thereof expresses CD36 and CD38; 100% of blastic plasmacytoid dendritic cell neoplasm express CD4, while for other rare lymphohematopoietic tumors, 95% or more expresses HLA-ABC and 90% or more expresses CD38; whereas, the majority of non-hematopoietic tumors do not express these markers, and the CD3/CD4/CD19/CD36/CD38/HLA-ABC combination in the present invention can essentially exclude $CD45^-/CD56^+$ or $CD45^-/CD56^-$ lymphohematopoietic tumors.

2) Exclusion of non-specific staining: false positives may occur with a low detection ratio, and thus CD9 and CD81 are used for further confirmation when $CD45^-/CD56^+$ and/or $GD2^+$, $CD45^-/CD56^+$ and/or cytokeratin$^+$, and $CD45^-/CD56^-/GD2^-/$cytokeratin$^-/CD36^-/$HLA-ABC$^-$ cells are present, and non-hematopoietic tumors are suspected, especially when the tumor cells do not express CD56, GD2, and cytokeratin. Non-specific staining is in many cases caused by platelets, nucleated erythroid cells, and dead cells, and the vast majority of these false positive cells expresses CD36. The use of the CD9/CD81/CD36 combination in the present invention allows efficient exclusion of non-specific staining.

3) Prevention of missed diagnosis: due to the wide variety of non-hematopoietic tumors, their complex origin and the great heterogeneity of immunophenotypes, caution is to be taken to prevent $CD45^-/CD56^-/GD2^-/$cytokeratin$^-$ tumors being missed. CD36 and/or HLA-ABC in combination with CD45 are used to set up gates in this invention, and if $CD45^-/CD56^-/GD2^-/$cytokeratin$^-/CD36^-/HLA\text{-}ABC^-$ cells are present, non-hematopoietic tumors are highly suspected.

4) Further determination of subtypes: non-hematopoietic tumors are mainly divided into those of neuromuscular origin and epithelial origin, 95% or more of tumors of neuromuscular origin expresses CD56 but not cytokeratin; among them, neuroblastoma is the most common non-hematopoietic tumor that expresses GD2, CD9, and CD81, wherein GD2 has relatively high specificity, while CD9 and CD81 have poor specificity and are found in many lymphohematopoietic cells and non-hematopoietic cells. 90% or more of epithelial-derived non-hematopoietic tumors express cytokeratin, with a CD56 expression rate of 55-78%. It is nonetheless noteworthy that cytokeratin is a large family consisted of more than 20 subunits, and different kinds of epithelial-derived tumors express different subunits. In the present invention, a cytokeratin antibody complex including CK8, CK18, and CK19 monoclonal antibodies is selected, which has a coverage as high as 94.59%. For further determination of subtypes, given the similarity of immunophenotypes of non-hematopoietic tumors of the same origin, determination needs to be made in relation to the clinical lesion site. Nevertheless, the main tasks of flow cytometry are screening (to find the tumor), diagnosis (to exclude other possibilities, including auxiliary diagnosis), and detection at post-treatment follow-up. The treatment of different subtypes of tumors in the same category is similar, and therefore the protocol of the present invention can meet the clinical needs.

In summary, the present invention provides a reagent composition for screening and/or diagnosis and follow-up of non-hematopoietic tumors and the use thereof. The advantages of the present invention are as follows: (1) based on the knowledge of a large number of lymphohematopoietic tumors, non-hematopoietic tumors, normal cells and the like, a very comprehensive, highly sensitive and specific, and particularly practical protocol is designed, and the rate of missed diagnosis is minimized; (2) in application, follow-ups, i.e., the detection of minimal residual diseases, are very challenging in current diagnostic techniques for non-hematopoietic tumors, while the gating with a complex combination of multiple markers in the present protocol is of great significance as it helps in post-treatment follow-up, in addition to preventing missed diagnosis; (3) the present invention adopts a screening/diagnosis and follow-up protocol with extremely wide coverage, and premixed antibodies may be used once the protocol is established, which enhances standardization, reduces variation among labs, facilitates commercialization, improves efficiency and the rate accurate diagnosis, and has great social significance; (4) upon standardization and generalization of the protocol, a pipeline work of sample processing, machine acquisition, and data analysis may be facilitated to achieve automation, which creates rooms for the development of artificial intelligence in the future; (5) although flow cytometry has been introduced to clinical diagnosis for three or four decades, it was rarely associated with non-hematopoietic tumors which have the highest morbidity and pose the biggest threat to human beings, much less a highly effective standardized detection protocol that is applicable to all populations; therefore, the present invention is a detection and analysis protocol for screening/diagnosis and follow-up of non-hematopoietic tumors that is urgently needed by the society and in the clinical setting, and is very suitable for widespread application and promotion; and (6) in the present invention, with each tube having its own focus, diagnostic and differential diagnostic indicators are provided in each tube, which objectively achieves: 1) simultaneous diagnosis and differential diagnosis; 2) exclusion of false positives resulted from non-specific staining in very rare cases; 3) prevention of missing non-hematopoietic tumors that are negative for all of GD2, cytokeratin, and CD56; and 4) because the differentiation between various lymphohematopoietic and non-hematopoietic tumors is involved, that the markers such as HLA-ABC, CD36 and CD38, which are mainly found in lymphohematopoietic tumors (including CD45-negative lymphohematopoietic cells), are proposed for the very first time for use in the diagnosis and differential diagnosis of non-hematopoietic tumors.

DETAILED DESCRIPTION OF THE INVENTION

For better understanding of the technical features, objectives and beneficial effects of the present invention, the technical solutions of the present invention are hereinafter described in details, but it is not to be construed as limitation to the implementable scope of the present invention.

Example 1. Preparation of Reagents

The combination of antibodies used in this example was:

A first set of antibody components of: an anti-CD9 antibody, an anti-GD2 antibody, an anti-CD3 antibody, an anti-CD4 antibody, an anti-CD56 antibody, an anti-CD36 antibody, an anti-CD81 antibody, and an anti-CD45 antibody, with each antibody being fluorescein labeled with FITC, PE, PerCP-Cy5.5, PE-Cy7, APC, APC-Cy7, BV421, and V500, respectively; the above eight monoclonal antibody reagents were mixed in a first container in a volume ratio of 5:5:5:3:2:3:3:3.

A second set of antibody components of: an anti-HLA-ABC antibody, an anti-CD38 antibody, an anti-CD19 antibody, an anti-CD56 antibody, an anti-CD36 antibody, an anti-CD7 antibody, and an anti-CD45 antibody, with each antibody being fluorescein labeled with PE, PerCP-Cy5.5, PE-Cy7, APC, APC-Cy7, BV421, and V500, respectively; the above seven monoclonal antibody reagents were mixed in a second container in a volume ratio of 5:5:3:2:3:3:3.

A third set of antibody components of: anti-cytoplasmic cytokeratin (CK) antibodies, fluorescein-labeled with FITC, which was contained in a third container.

Each of the antibodies in this example is commercially available; among them, the anti-cytoplasmic cytokeratin (CK) antibodies are a product of Miltenyi Biotec, Germany (clone number: CK3-6H5), which is a complex composed mainly of CK8, CK18 and CK19 monoclonal antibodies, and the rest of the directly fluorescein-labeled antibodies are products of Becton Dickinson, USA.

Optionally, haemolysin was prepared and contained in a fourth container, solution A of a permeabilization reagent in a fifth container, solution A of the permeabilization reagent in a sixth container, and PBS buffer in a seventh container. The haemolysin, permeabilization reagent and PBS buffer are commercially available; among them, the cell lysing solution and permeabilization reagent are products from Becton Dickinson, USA, and the PBS buffer is from Beckman Coulter, Inc.

Example 2. Sample Processing

The samples were processed by using the sets of antibodies of Example 1.

According to the cell counting results, a sample was added to a first flow cytometric tube to ensure that the amount of cells added was about $2'10^6$. Then 29 μL of eight different fluorescein-labeled cytosolic monoclonal antibody reagents were added to the flow cytometric tube according to Table 1, mixed thoroughly with the cell suspension and incubated for 15 minutes at room temperature in dark. 3 ml of 1× hemolysin was added and incubated for 10 minutes in dark to lyse the red blood cells. After centrifugation at 1500 rpm for 5 minutes to remove the supernatant, 3 ml of PBS buffer was added and mixed evenly, and the supernatant was removed by centrifugation at 1500 rpm for 5 minutes. Then 0.5 ml PBS buffer was added to resuspend the cells to obtain a processed sample ready for machine assay.

According to the cell counting results, a sample was added to a second flow cytometric tube to ensure that the amount of cells added was about $2\times10^6$. Then 24 μL of seven different fluorescein-labeled cytokeratin monoclonal antibody reagents were added to the flow cytometric tube according to Table 1, mixed thoroughly with the cell suspension and incubated for 15 minutes at room temperature in dark. 100 μL of a solution A of a permeabilization reagent was added, and incubated for 5 minutes at room temperature in dark. 3 ml of 1× hemolysin was added and incubated for 10 minutes in dark to lyse the red blood cells. After centrifugation at 1500 rpm for 5 minutes to remove the supernatant, 50 μL of a solution B of a permeabilization reagent and 50 μL, of the cytoplasmic monoclonal antibody reagent cytokeratin (CK)-FITC were added, incubated for 15 minutes at room temperature in dark. Finally, 3 ml of PBS buffer was added and mixed evenly, and the supernatant was removed by centrifugation at 1500 rpm for 5 minutes. Then 0.5 ml PBS buffer was added to resuspend the cells to obtain a processed sample ready for machine assay.

TABLE 1

Antibody composition for screening/diagnosis
and follow-up of non-hematopoietic tumors

|  | First tube | | Second tube | | |
| --- | --- | --- | --- | --- | --- |
| Fluorescein | First container | Amount (μL) | Second container | Third container | Amount (μL) |
| FITC | CD9 | 5 | \ | Cytokeratin (CK) | 5 |
| PE | GD2 | 5 | HLA-ABC | \ | 5 |
| PerCP-Cy5.5 | CD3 | 5 | CD38 | \ | 5 |
| PE-CY7 | CD4 | 3 | CD19 | \ | 3 |
| APC | CD56 | 2 | CD56 | \ | 2 |
| APC-Cy7 | CD36 | 3 | CD36 | \ | 3 |
| BV421 | CD81 | 3 | CD7 | \ | 3 |
| V500 | CD45 | 3 | CD45 | \ | 3 |

Example 3. Sample Assaying

Samples processed according to the method of Example 2 were assayed on a 3-laser 10-color FACS Canto plus flow cytometer from Becton Dickinson, USA, with preferably 1 million cells per tube (at least 300,000 recommended) acquired before the data were analyzed by using a Diva 2.8 software or other software such Kaluza.

Here, gates for the flow cytometry assay were set as follows:
1) fixed gating: a single cell gate, a live cell gate, and blood cell gates were sequentially set up; 2) multi-marker combination gating: starting from single live cells, all cells needed to be gated and defined in parallel with blood cell gates; 3) within the gates set with the multi-marker combination, tumor cells were identified when cells that were not normally present appeared; 4) other CD45-negative, CD56-positive or negative lymphohematopoietic tumors, and other possible non-specific staining were excluded, and a diagnosis was made; and 5) differentiation of common subtypes was done based on the expression of GD2 and cytokeratin.

1. Fixed gating: consisted of an adherent cell removal gate, live cell gate, and blood cell gates, which were present in a tandem fashion.

Adherent cell removal gate: an adherent cell removal gate (often denoted as P1) was first set by using the area (A) and height (H) from forward scattering (FSC), and the adherent cells could be removed by FSC-Area (A)/Height (H), based on the principle that A and H are positively correlated for a spherical cell (See the first panel in FIGS. 1 to 6).

Live cell gate: for cells within P1, live cell gates (often denoted as P2) were set up by using FSC/side scattering (SSC) to obtain single live cells. The principle of FSC/SSC is that live cells are sub-normally distributed in size and granularity, clustered around a center with clear boundaries from dead cells, apoptotic cells, debris and background noise (see the second panel in FIGS. 1 to 6).

Blood cell gates: Within the single live cell gates (P2 gates), blood cell gates were normally set first with CD45/SSC, for a preliminary observation of lymphocytes, monocytes, granulocytes, nucleated red blood cells, and the presence of obvious tumor cells or abnormal cells. Various populations of blood cells were roughly differentiated by CD45/SSC, based on the principle of the difference in fluorescence intensity of CD45 expression of hematopoietic cells (mature lymphocytes>monocytes>granulocytes>nucleated erythrocytes) and the difference in SSC size (eosinophils>granulocytes>monocytes>mature lymphocytes>nucleated erythrocytes) (see the third panel in FIGS. 1 to 6). The purpose was to prevent missing large tumor cell populations after missed diagnosis or tumor evolution, and also to set up internal control.

2. Initial targeting of suspicious cells by multi-marker combination gating: performed in parallel with the CD45/SSC gating, starting with a single live cell (P2). For the first tube, a gate NH1 was set with CD45/CD56 antibodies to detect CD45$^-$/CD56$^+$ cells, which could screen for the vast majority of non-hematopoietic tumors (96.65% based on statistics of the present invention); a gate NH2 was set with CD45/GD2 antibodies to detect CD45$^-$/GD2$^+$ cells, which were mainly found in neuroblastoma and most types of melanomas and were expressed to a varying extent in other bone and soft tissue tumors, small cell lung cancer, and brain tumors. Within the gate P2, for the second tube, a gate NH4 was set with CD45/CD56 antibodies to detect CD45$^-$/CD56$^+$ cells, which could screen for the vast majority of non-hematopoietic tumors, and a gate NH5 was set with CD45/cytoplasmic cytokeratin antibodies detects CD45$^-$/cytokeratin$^+$ cells, which were mainly found in epithelial-derived tumor cells (based on the investigation of cell lines and clinical sample assaying according to the present invention, there was a CD45$^-$/cytokeratin$^+$ positivity rate of 94.59% in tumor cells of epithelial origin).

3. Prevention of missed diagnosis by using further universal markers for lymphohematopoietic cells within gate P2: within the gate P2, for both the first and second tubes, CD45/CD36 was used to set a gate NH3 (the first tube) and a gate NH6 (the second tube), respectively, to determine the presence of CD45$^-$/CD36$^-$ cells; the expressions of CD9/GD2/CD56/CD81 cells in the gate NH3 (the first tube) and cytokeratin/HLA-ABC/CD38/CD56 cells in the gate NH6 (the second tube) were displayed, and the omission of CD45$^-$/GD2$^-$/CD56$^-$/cytokeratin$^-$ non-hematopoietic tumor cells was prevented, with the majority of these tumors showing CD81$^+$ and/or CD9$^+$ as well as HLA-ABC$^-$/CD38$^-$/CD36$^-$.

4. Further exclusion of CD45-negative lymphohematopoietic tumor cells and subtype diagnosis: in the first tube, the expressions of CD3/CD4/CD36/CD9/CD81 in the cells within the gates NH1 and NH2 were displayed, and the following cells were excluded: CD3$^+$ T cells, CD4$^+$ T cells, CD4dim monocytes or blastic plasmacytoid dendritic cells, CD36$^+$ nucleated red blood cells, megakaryocytes and monocytes; in the second tube, the expressions of HLA-ABC/CD38/CD19/CD36/CD7 in the cells within the gates NH4 and NH5 were displayed, and CD38-positive benign and malignant plasma cells, various acute leukemia cells and the like, CD19$^+$ B cells and/or plasma cells, CD36$^+$ nucleated erythrocytes, megakaryocytes and monocytes, CD7$^+$ T cells, NK cells and other dendritic cell tumors with abnormal CD7 expression and acute myeloid leukemia and the like were excluded; all of these lymphohematopoietic cells with 99% or more as shown by experimental data of the present invention, express HLA-ABC almost exclusively, except for nucleated erythrocytes where 95% or more expresses CD36. Determination of subtypes was made based on the GD2 expression in the first tube and the cytokeratin expression in the second tube: GD2 was mainly found in neuroblastoma as well as some melanomas and other embryonal tumors, and cytokeratin was mainly found in non-hematopoietic tumors of epithelial origin.

In the present invention, by comparing each cell population as shown with the corresponding normal cells within the multi-marker combination gates, tumor cells are identified, lymphohematopoietic tumors are excluded, and the nature of the non-hematopoietic tumors was determined.

In short, the present invention covers as many common and rare non-hematopoietic tumors of all ages as possible with the multi-marker combination gating, and universal markers for lymphohematopoietic tumors are identified, and lymphohematopoietic tumors and non-specific staining are ingeniously excluded by using these markers, and missed diagnosis of non-hematopoietic tumors that do not express GD2 and cytokeratin is prevented. Here, the non-hematopoietic tumors are most types of solid tumors other than lymphohematopoietic tumors as published by the World Health Organization, including: tumors of malignant epithelial origin (e.g., lung cancer, breast cancer, gallbladder cancer, colon cancer, prostate cancer, esophageal cancer, fallopian tube cancer, head and neck cancer, liver blastoma, pancreaticoblastoma, pancreatic cancer, etc.), embryonal tumors (neuroblastoma, retinoblastoma, germ cell tumor, medulloblastoma, primitive neuroectodermal tumor (PNET), etc.), soft tissue tumors and extraosseous sarcomas (Ewing sarcoma, rhabdomyosarcoma, etc.), bone tumors and cartilage tumors (osteosarcoma, soft tissue sarcoma, etc.), malignant kidney tumors (nephroblastoma, adrenal carcinoma, renal clear cell carcinoma, etc.), malignant melanoma and the like.

Figure 1:
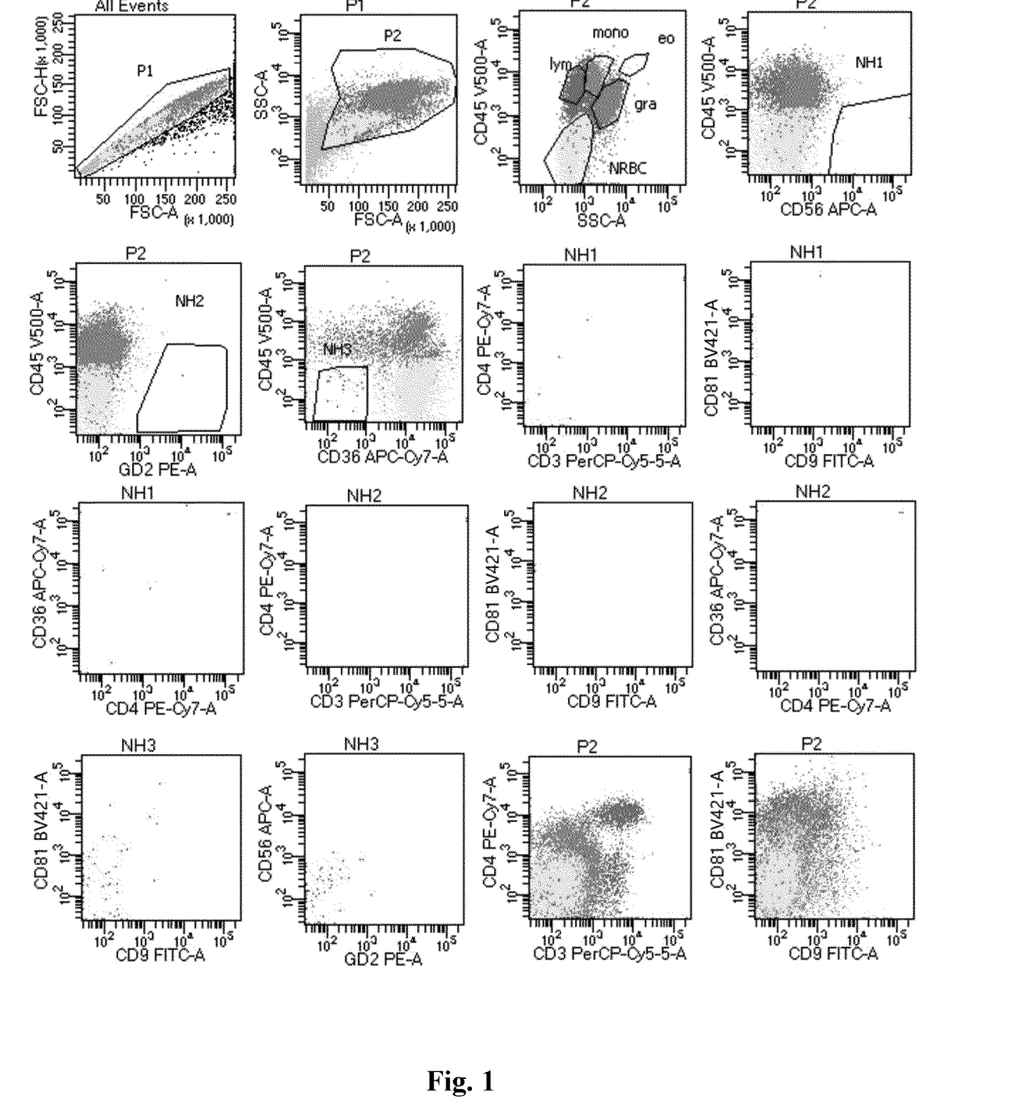
FIGS. 1 to 2 show the results of flow cytometry gating and analysis of normal bone marrow samples in a specific embodiment of the present invention.
Figure 2:
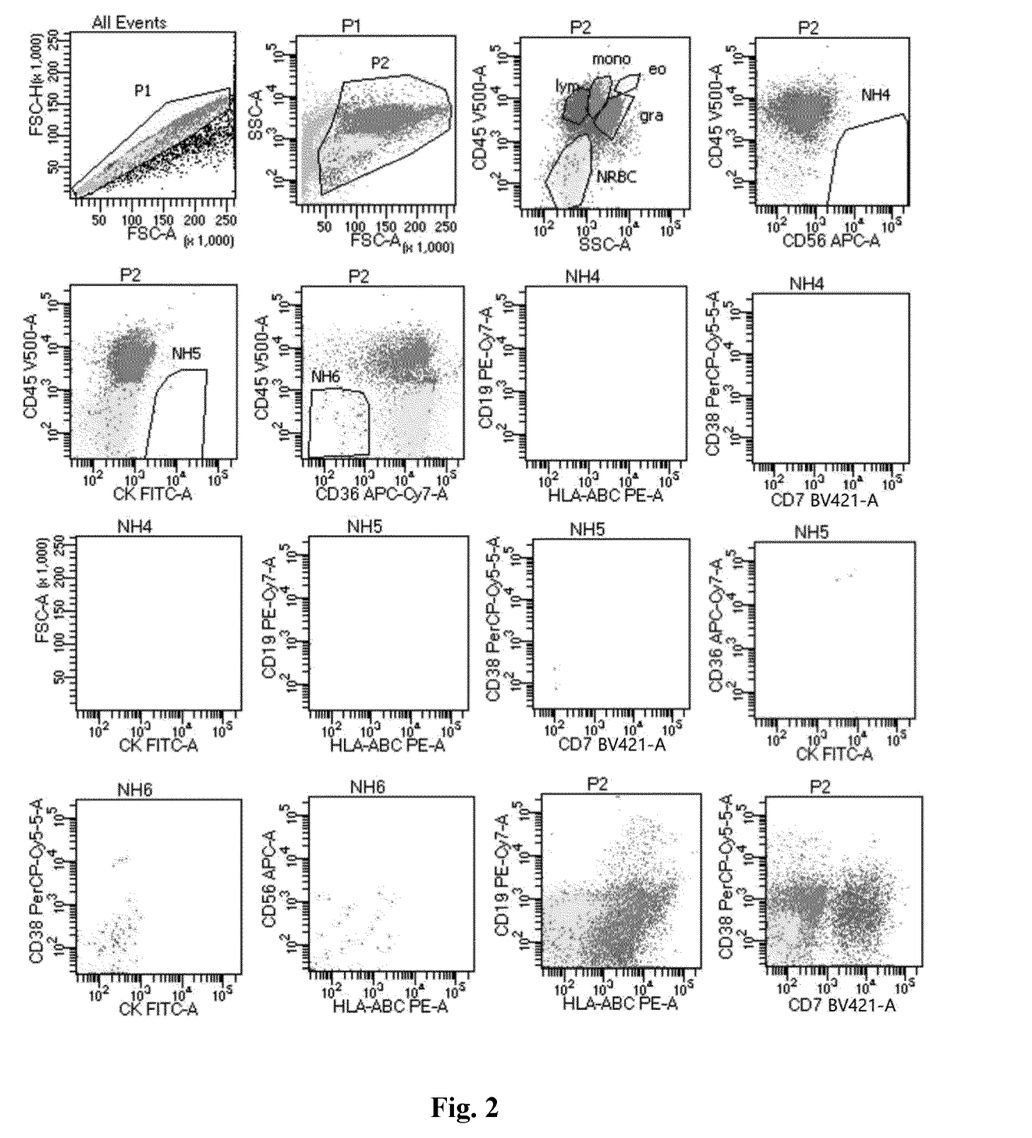

Specifically, FIGS. 1-2: normal bone marrow sample from the same case, with the 2 tubes analyzed together.

More specifically, FIG. 1 shows the analysis of the normal bone marrow sample in the first tube. The following was done sequentially: 1) P1 was set as an adherent cell removal gate with FSC-A/H to obtain single cells in P1; 2) P2 was set as a live cell gate within P1 by showing FSC/SSC to obtain single live cells in P2; 3) within the gate P2, blood cell gates were set with CD45/SSC to obtain lymphocytes (lym), granulocytes (gra), monocytes (mono), nucleated erythrocytes (NRBC), and eosinophil (eo) gates; 4) within the gate P2, a gate NH1 was set with CD45/CD56 to screen CD45$^-$/CD56$^+$ tumor cells, which were absent in this normal sample; 5) a gate NH2 was set with CD45/GD2 antibodies to detect CD45$^-$/GD2$^+$ cells, which were absent in this normal sample; 6) within the gate P2, a gate NH3 was set with CD45/CD36 to determine the presence of CD45$^-$/CD36$^-$ cells, which were absent in this normal sample; 7) the expressions of CD3/CD4/CD36/CD9/CD81 in the cells within the gates NH1 and NH2 were displayed, and CD3$^+$ T cells, CD4$^+$ T cells, CD4dim monocytes or blastic plasmacytoid dendritic cells, CD36$^+$ nucleated erythrocytes, megakaryocytes and monocytes were excluded, which were absent in this normal sample; 8) the expressions of CD9/GD2/CD56/CD81 in the cells within the gate NH3 were displayed, the omission of CD45$^-$/GD2$^-$/CD56$^-$/CD36$^-$ non-hematopoietic tumor cells was prevented; most of these tumors express CD81$^+$ and/or CD9$^+$, which was absent in this normal sample.

Specifically, FIG. 2 shows the analysis of the normal bone marrow sample in the second tube (in the figure, cytokeratin is abbreviated as CK). The following was done sequentially: 1) P1 was set as an adherent cell removal gate with FSC-A/H to obtain single cells in P1; 2) P2 was set as a live cell gate within P1 by showing FSC/SSC to obtain single live cells in P2; 3) within the gate P2, blood cell gates were set with CD45/SSC to obtain lymphocytes (lym), granulocytes (gra), monocytes (mono), nucleated erythrocytes (NRBC), and eosinophil (eo) gates; 4) within the gate P2, a gate NH4 was set with CD45/CD56 antibodies to detect CD45$^-$/CD56$^+$ tumor cells, which were absent in this normal sample; 5) within the gate P2, a gate NH5 was set with CD45/cytoplasmic cytokeratin antibodies to detect CD45$^-$/cytokeratin$^+$ cells, which were absent in this normal sample; 6) within the gate P2, a gate NH6 was set with CD45/CD36 to determine the presence of CD45$^-$/CD36$^-$ cells, which were absent in this normal sample; 7) the expressions of HLA-ABC/CD38/CD19/CD36/CD7 in the cells within the gates NH4 and NH5 were displayed, and CD38-positive benign and malignant plasma cells, various acute leukemia cells and the like, CD19$^+$ B cells and/or plasma cells, CD36$^+$ nucleated erythrocytes, megakaryocytes and monocytes, CD7$^+$ T cells, NK cells and other dendritic cell tumors with abnormal CD7 expression and acute myeloid leukemia and the like were excluded, which were absent in this normal sample; 8) the expressions of cytokeratin/HLA-ABC/CD38/CD56 in the cells within the gate NH6 were displayed, the omission of CD45$^-$/cytokeratin$^-$/CD56$^-$/CD36$^-$ non-hematopoietic tumor cells was prevented, which was absent in this normal sample.

Figure 3:
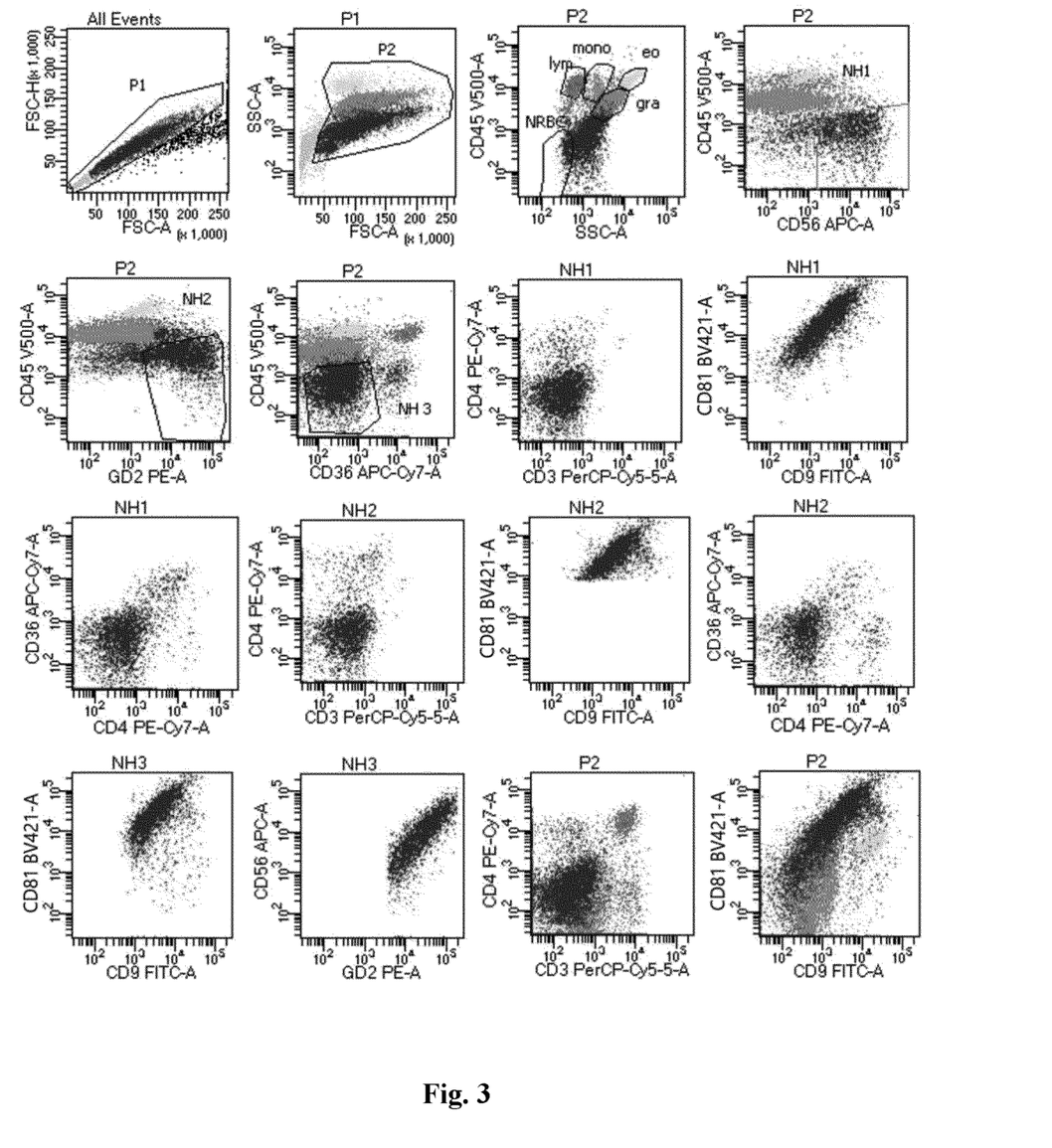
FIGS. 3 to 4 show the results of flow cytometry gating and analysis of bone marrow samples from neuroblastoma in a specific embodiment of the present invention.
Figure 4:
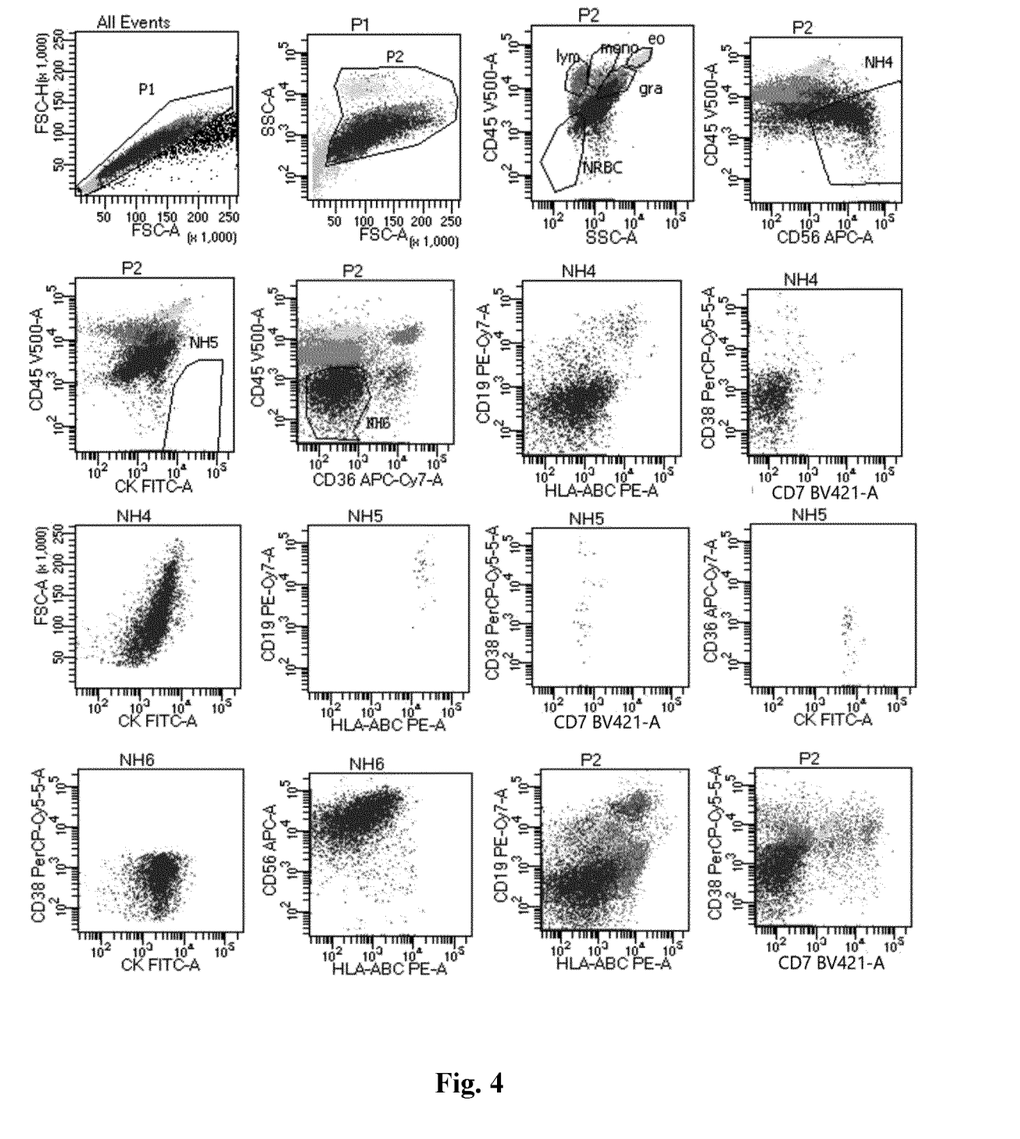

Specifically, FIGS. 3-4 show the immunotyping in the first and second tubes of the bone marrow sample from the same neuroblastoma patient.

Specifically, FIG. 3 shows the analysis of the first tube of the bone marrow sample from the neuroblastoma patient. The following was done sequentially: 1) P1 was set as an adherent cell removal gate with FSC-A/H to obtain single cells in P1; 2) P2 was set as a live cell gate within P1 by showing FSC/SSC to obtain single live cells in P2; 3) within the gate P2, blood cell gates were set with CD45/SSC to obtain lymphocytes (lym), granulocytes (gra), monocytes (mono), nucleated erythrocytes (NRBC), and eosinophil (eo) gates; 4) within the gate P2, a gate NH1 was set with CD45/CD56 to screen CD45$^-$/CD56$^+$ tumor cells, and 13.2% of the cells (in nucleated cells, dark gray cell population) expressing CD45$^-$/CD56$^+$ were found in this sample; 5) a gate NH2 was set with CD45/GD2 antibodies to detect CD45$^-$/GD2$^+$ cells, and 13.2% of the cells (in nucleated cells, dark gray cell population) expressing CD45$^-$/GD2$^+$ were found in this sample; 6) within the gate P2, a gate NH3 was set with CD45/CD36 to determine the presence of CD45$^-$/CD36$^-$ cells, and 13.2% of the cells (in nucleated cells, dark gray cell population) was found CD45$^-$/CD36$^-$ in this sample; 7) the expressions of CD3/CD4/CD36/CD9/CD81 in the cells within the gates NH1 and NH2 were displayed, and CD3$^+$ T cells, CD4$^+$ T cells, CD4dim monocytes or blastic plasmacytoid dendritic cells, CD36$^+$ nucleated erythrocytes, megakaryocytes and monocytes were excluded, and 13.2% of the cells (in nucleated cells, dark gray cell population) not expressing CD3, CD4, and CD36, but expressing CD9 and CD81, was found in this sample; 8) the expressions of CD9/GD2/CD56/CD81 in the cells within the gate NH3 were displayed, and the omission of CD45$^-$/GD2$^-$/CD56$^-$/CD36$^-$ non-hematopoietic tumor cells was prevented; 13.2% of cells (in nucleated cells, dark gray cell population) not expressing CD3, CD4, CD36, and CD45, but expressing CD9, CD81, GD2, and CD56, were found in this sample as non-hematopoietic tumor cells, with a high possibility of neuroblastoma, and the diagnosis was confirmed in combination with clinical and other laboratory assays.

Specifically, FIG. 4 shows the analysis of the second tube of the same bone marrow sample as in FIG. 3 (in the figure, cytokeratin is abbreviated as CK). The following was done sequentially: 1) P1 was set as an adherent cell removal gate with FSC-A/H to obtain single cells in P1; 2) P2 was set as a live cell gate within P1 by showing FSC/SSC to obtain single live cells in P2; 3) within the gate P2, blood cell gates were set with CD45/SSC to obtain lymphocytes (lym), granulocytes (gra), monocytes (mono), nucleated erythrocytes (NRBC), and eosinophil (eo) gates; 4) within the gate P2, a gate NH4 was set with CD45/CD56 antibodies to detect CD45$^-$/CD56$^+$ tumor cells, and 13.2% of the cells (in nucleated cells, dark gray cell population) expressing CD45$^-$/CD56$^+$ were found in this sample; 5) within the gate P2, a gate NH5 was set with CD45/cytoplasmic cytokeratin antibodies to detect CD45$^-$/cytokeratin$^+$ cells, which were absent in this sample; 6) within the gate P2, a gate NH6 was set with CD45/CD36 to determine the presence of CD45$^-$/CD36$^-$ cells, and 13.2% of the cells (in nucleated cells, dark gray cell population) expressing CD45$^-$/CD36$^-$ were found in this sample; 7) the expressions of HLA-ABC/CD38/CD19/CD36/CD7 in the cells within the gates NH4 and NH5 were displayed, and CD38-positive benign and malignant plasma cells, various acute leukemia cells and the like, CD19$^+$ B cells and/or plasma cells, CD36$^+$ nucleated erythrocytes, megakaryocytes and monocytes, CD7$^+$ T cells, NK cells and other dendritic cell tumors with abnormal CD7 expression and acute myeloid leukemia and the like were excluded; 13.2% of the cells (in nucleated cells, dark gray cell population) not expressing HLA-ABC, CD38, CD19, CD36, and CD7 were found in this sample; 8) the expressions of cytokeratin/HLA-ABC/CD38/CD56 in the cells within the gate NH6 were displayed, and the omission of CD45$^-$/cytokeratin$^-$/CD56$^-$/CD36$^-$ non-hematopoietic tumor cells was prevented; 13.2% of the cells (in nucleated cells, dark gray cell population) not expressing cytokeratin, HLA-ABC, CD38, CD19, CD36, CD7, and CD45, but expressing CD56, were found in this sample as non-hematopoietic tumor cells, with a high possibility of neuroblastoma, and the diagnosis was confirmed in combination with clinical and other laboratory assays.

Figure 5:
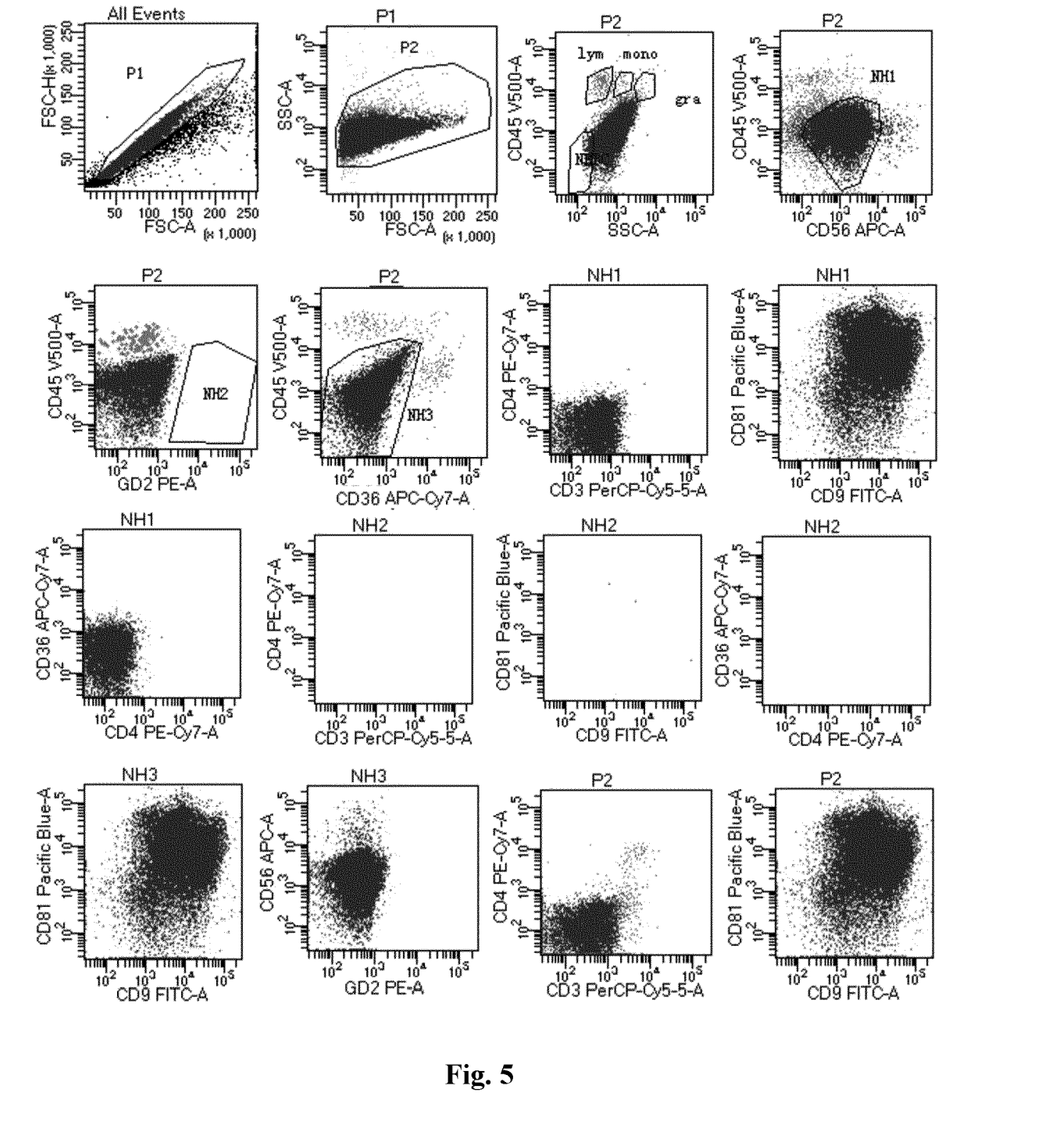
FIGS. 5 to 6 show the results of flow cytometry gating and analysis of bone marrow samples from epithelial-derived tumors (lung cancer) in a specific embodiment of the present invention.
Figure 6:
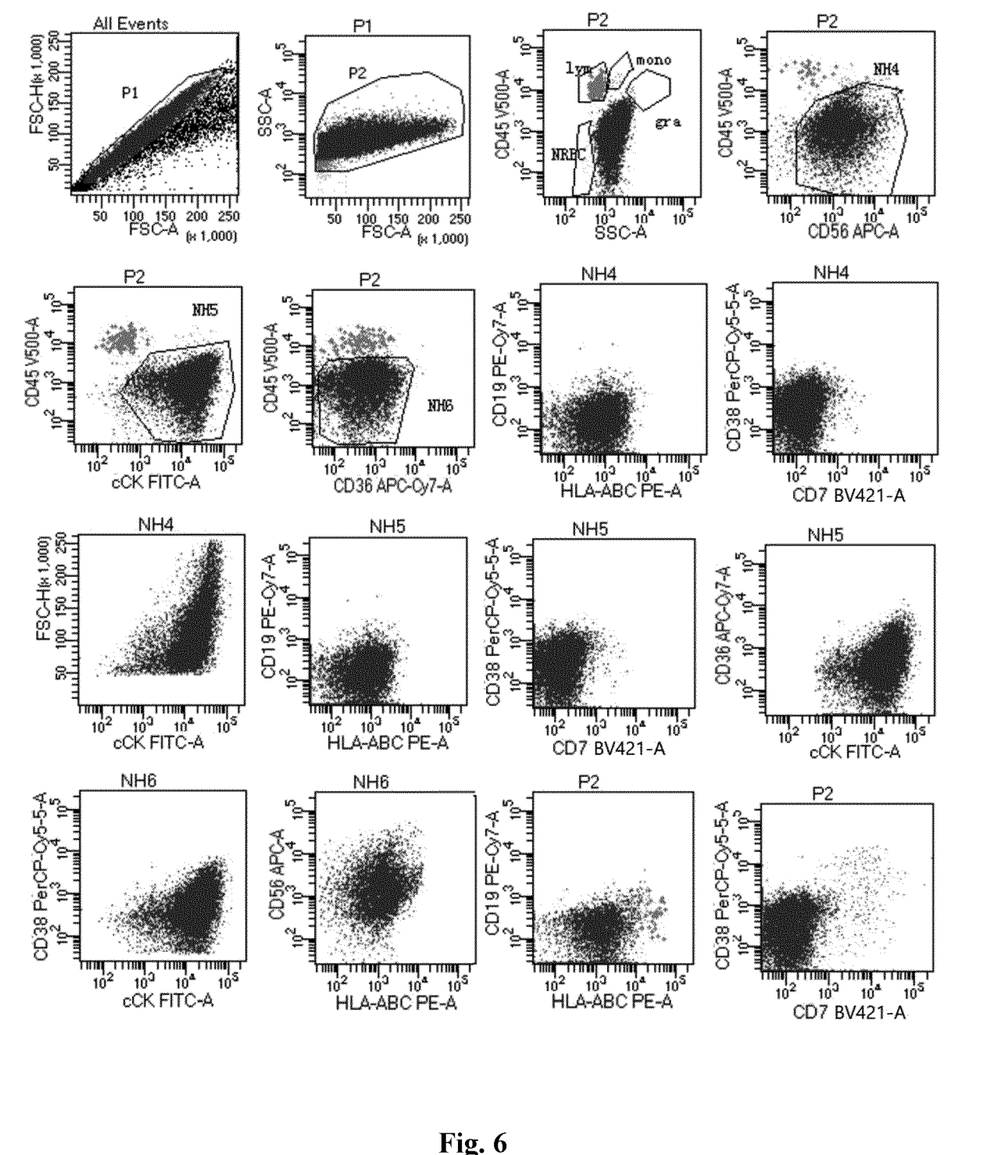

Specifically, FIGS. 5-6 show the immunotyping in the first and second tubes of the bone marrow sample from the same patient with non-hematopoietic tumor of epithelial origin (lung cancer).

Specifically, FIG. 5 shows the analysis of the bone marrow sample from the patient with non-hematopoietic tumor of epithelial origin (lung cancer) in the first tube. The following was done sequentially: 1) P1 was set as an adherent cell removal gate with FSC-A/H to obtain single cells in P1; 2) P2 was set as a live cell gate within P1 by showing FSC/SSC to obtain single live cells in P2; 3) within the gate P2, blood cell gates were set with CD45/SSC to obtain lymphocytes (lym), granulocytes (gra), monocytes (mono), nucleated erythrocytes (NRBC), and eosinophil (eo) gates; 4) within the gate P2, a gate NH1 was set with CD45/CD56 to screen CD45$^-$/CD56$^+$ tumor cells, and 94.10% of the cells (in nucleated cells, dark gray cell population) expressing CD45$^-$/CD56$^+$ were found in this sample; 5) a gate NH2 was set with CD45/GD2 antibodies to detect CD45$^-$/GD2$^+$ cells, which was not present in this sample; 6) within the gate P2, a gate NH3 was set with CD45/CD36 to determine the presence of CD45$^-$/CD36$^-$ cells, and 94.10% of the cells (in nucleated cells, dark gray cell population) was found CD45$^-$/CD36$^-$ in this sample; 7) the expressions of CD3/CD4/CD36/CD9/CD81 in the cells within the gates NH1 and NH2 were displayed, and CD3$^+$ T cells, CD4$^+$ T cells, CD4dim monocytes or blastic plasmacytoid dendritic cells, CD36$^+$ nucleated erythrocytes, megakaryocytes and monocytes were excluded, and 94.10% of the cells (in nucleated cells, dark gray cell population) not expressing CD3, CD4, and CD36, but expressing CD9 and CD81, was found in this sample; 8) the expressions of CD9/GD2/CD56/CD81 in the cells within the gate NH3 were displayed, and the omission of CD45$^-$/GD2$^-$/CD56$^-$/CD36$^-$ non-hematopoietic tumor cells was prevented; 94.10% of cells (in nucleated cells, dark gray cell population) not expressing CD3, CD4, CD36, GD2, and CD45, but expressing CD9, CD81, and CD56, were found in this sample as non-hematopoietic tumor cells.

Specifically, FIG. 6 shows the analysis of the bone marrow sample from the same patient with non-hematopoietic tumor of epithelial origin (lung cancer) as FIG. 5 in the second tube (in the figure, cytokeratin is abbreviated as CK). The following was done sequentially: 1) P1 was set as an adherent cell removal gate with FSC-A/H to obtain single cells in P1; 2) P2 was set as a live cell gate within P1 by showing FSC/SSC to obtain single live cells in P2; 3) within the gate P2, blood cell gates were set with CD45/SSC to obtain lymphocytes (lym), granulocytes (gra), monocytes (mono), nucleated erythrocytes (NRBC), and eosinophil (eo) gates; 4) within the gate P2, a gate NH4 was set with CD45/CD56 antibodies to detect CD45$^-$/CD56$^+$ tumor cells, and 94.10% of the cells (in nucleated cells, dark gray cell population) expressing CD45$^-$/CD56$^+$ were found in this sample; 5) within the gate P2, a gate NH5 was set with CD45/cytoplasmic cytokeratin antibodies to detect CD45$^-$/cytokeratin$^+$ cells, and 94.10% of the cells (in nucleated cells, dark gray cell population) expressing CD45$^-$/cytokeratin$^+$ were found in this sample; 6) within the gate P2, a gate NH6 was set with CD45/CD36 to determine the presence of CD45$^-$/CD36$^-$ cells, and 94.10% of the cells (in nucleated cells, dark gray cell population) expressing CD45$^-$/CD36$^-$ were found in this sample; 7) the expressions of HLA-ABC/CD38/CD19/CD36/CD7 in the cells within the gates NH4 and NH5 were displayed, and CD38-positive benign and malignant plasma cells, various acute leukemia cells and the like, CD19$^+$ B cells and/or plasma cells, CD36$^+$ nucleated erythrocytes, megakaryocytes and monocytes, CD7$^+$ T cells, NK cells and other dendritic cell tumors with abnormal CD7 expression and acute myeloid leukemia and the like were excluded; 94.10% of the cells (in nucleated cells, dark gray cell population) not expressing HLA-ABC, CD38, CD19, CD36, and CD7 were found in this sample; 8) the expressions of cytokeratin/HLA-ABC/CD38/CD56 in the cells within the gate NH6 were displayed, and the omission of CD45$^-$/cytokeratin$^-$/CD56$^-$/CD36$^-$ non-hematopoietic tumor cells was prevented; 94.10% of the cells (in nucleated cells, dark gray cell population) not expressing HLA-ABC, CD38, CD19, CD36, CD7, and CD45, but expressing cytokeratin and CD56, were found in this sample as non-hematopoietic tumor cells, with a high possibility of epithelial origin, and a bone marrow involvement of lung cancer was contemplated in combination with clinical history.

The process of development of this protocol and clinical validation by using the method of this example: this study was started at the Hebei Yanda Lu Daopei Hospital in 2008, and by Mar. 31, 2022, 858 samples from 850 individuals were assayed: 476 males and 374 females, with a median age of 4 (aged 0 to 80); 792 of them were of age 14 or younger, and 58 were older than 14 years old. Of the 858 samples, 617 were bone marrow samples, 3 were peripheral blood samples, 196 were cerebrospinal fluid samples, 9 were thoracoabdominal fluid samples, 3 were lymph node dissection samples, and 30 were various tissue puncture samples. Among them, 575 showed positive results and 283 showed negative results, which were 90% or more consistent with other laboratory assays and clinical diagnosis.

The assay results of the 575 positive samples were analyzed, of which 8 were follow-up samples at different time points, and the one with highest percentage was selected for analysis. Thus, a total of 567 samples from 567 individuals were analyzed, 319 males and 248 females, with a median age of 4 (aged 0-80). The median tumor cell ratio was 0.16% (0.01%-96.23%), for 442 bone marrow samples, 2 peripheral blood samples, 84 cerebrospinal fluid samples, 9 thoracoabdominal fluid samples, 2 lymph node dissection samples, and 28 of various tissue puncture materials. Almost all tumor types indicated in WHO diagnostic criteria were covered (see Table 2).

TABLE 2

Types of diseases involved in assayed positive samples for non-hematopoietic tumors at Lu Dao Pei Hospital from 2008 to March 2022

| Type | Subtype | Number of cases |
| --- | --- | --- |
| Malignant tumors of epithelial origin | Lung Cancer | 10 |
|  | Breast cancer, gallbladder cancer, colon cancer, prostate cancer, esophageal cancer, fallopian tube cancer, head and neck cancer, hepatoblastoma, pancreatoblastoma, pancreatic cancer, etc. | 36 |
| Embryonal tumors | Neuroblastoma | 381 |
|  | Retinoblastoma | 71 |
|  | Germ cell tumor | 1 |

TABLE 2-continued

Types of diseases involved in assayed positive samples for non-hematopoietic tumors at Lu Dao Pei Hospital from 2008 to March 2022

| Type | Subtype | Number of cases |
| --- | --- | --- |
|  | Medulloblastoma | 9 |
|  | Primitive neuroectodermal tumor (PNET), etc. | 7 |
| Soft tissue tumors and extraosseous sarcomas | Ewing Sarcoma | 6 |
|  | Rhabdomyosarcoma | 16 |
|  | Other | 3 |
| Bone and cartilage tumors |  | 3 |
| Malignant kidney tumors |  | 16 |
| Malignant melanoma |  | 8 |

Immunophenotypic analysis of the 567 samples (Table 3): the predominant phenotypes were CD45 negative (100%), CD56 positive (96.65%), CD36 negative (100%), HLA-ABC negative (93.10%), CD81 positive (98.52%), and CD38 negative (95.40%), with relatively poor sensitivity of CD9 and CD99 of 75% and 58.86%, respectively. The rate of expression of other specific lymphohematopoietic markers, CD4, CD3, CD19, and CD7, was all zero. $CD45^-/CD56^+$ had a 96.65% coverage, with CD56-negative cases mainly seen in tumor cells of epithelial origin, and the expression rate of cytokeratin (CK) in this type was up to 94.59%. GD2 expression in neuroblastoma was 93.21%, but the specificity for the differentiation of subtypes was relatively poor, with a positive rate of 76.7% in other subtypes.

TABLE 3

Immunophenotypic analysis of non-hematopoietic tumors of 567 cases

|  | HLA-ABC | CD56 | CD45 | CD81 | CD9 |
| --- | --- | --- | --- | --- | --- |
| Total positive rate | 6.9% (30/434) | 96.65% (548/567) | 0 (0/567) | 98.52% (533/541) | 75% (384/512) |
| Positive rate of neuroblastoma | 6.13% (20/326) | 99.21% (378/381) | 0 (0/381) | 98.66% (368/373) | 78.93% (281/356) |
| Positive rate of tumors of epithelial origin | 8.82% (3/34) | 55.88% (19/34) | 0 (0/46) | 88.89% (16/18) | 70.59% (12/17) |
| Positive rate of other subtypes | 9.46% (7/74) | 99.34% (151/152) | 0 (0/140) | 99.33% (149/150) | 65.47% (91/139) |

|  | GD2 | cytokeratin | CD38 | CD99 | CD36 |
| --- | --- | --- | --- | --- | --- |
| Total positive rate | 85.71% (342/399) | 8.95% (35/391) | 4.6% (6/130) | 58.86% (206/350) | 0 (0/144) |
| Positive rate of neuroblastoma | 93.21% (261/280) | 0 (0/284) | 5.62% (5/89) | 557.03% (142/249) | 0 (0/77) |
| Positive rate of tumors of epithelial origin | 12.5% (2/16) | 94.59% (35/37) | 0 (0/12) | 75% (6/8) | 0 (0/13) |
| Positive rate of other subtypes | 76.7% (79/103) | 0 (0/71) | 3.45% (1/29) | 62.37% (58/93) | 0 (0/54) |

To further analyze the expression of these markers in the lymphohematopoietic system, 72 additional non-tumor bone marrow samples were additionally selected for the detection of the above markers, and CD45$^-$/CD56$^+$ or GD2$^+$ or cytokeratin$^+$ or CD45$^-$/CD56$^-$/GD2$^-$/cytokeratin$^-$/CD36$^-$/HLA-ABC$^-$ cells were not present in any of these samples.

Compared with the studies of the prior art, an important breakthrough of the present invention is the finding of non-lineage-specific markers that are very highly expressed in lymphohematopoietic tumors but rarely expressed in non-hematopoietic ones for screening and differential diagnosis, mainly including HLA-ABC, CD36, and CD38, based on the wide variety of types and big phenotypic differences in the diagnosis of non-hematopoietic tumors.

In order to further validate the efficiency of HLA-ABC identification among the specific markers of the present invention, the present inventors selected samples that had been immunophenotyped in the flow cytometry laboratory at the Hebei Yanda Lu Daopei Hospital from Aug. 1, 2016 to Oct. 30, 2021, for an HLA-ABC expression rate study. The samples included: 272 non-tumor samples, with 146 males and 126 females having a median age of 31 (aged 0-87), in which 268 were bone marrow samples, 1 was a peripheral blood sample, and 3 was tissue samples; 869 lymphohematopoietic tumors, with 544 males and 325 females having a median age of 28 (aged 0-85), in which 845 were bone marrow samples, 19 were peripheral blood samples, 7 were tissue puncture samples, and 1 was a thoracoabdominal fluid sample. All the diseases in the WHO lymphohematopoietic tumor category were covered (1 case of acute undifferentiated leukemia, 14 cases of mixed phenotype acute leukemia, 258 cases of acute B-lymphoblastic leukemia, 417 cases of acute myeloid leukemia, 83 cases of acute T-lymphoblastic leukemia, 10 cases of myeloproliferative neoplasm, 44 cases of myelodysplastic syndrome, 6 cases of myelodysplastic syndrome/myeloproliferative neoplasms, 11 cases of multiple myeloma, 18 cases of mature B-cell lymphoma, 5 cases of mature T-cell lymphoma, and 2 cases of mature NK-cell lymphoma. The HLA-ABC expression rate was found to be 100% in normal hematopoietic cells, except for nucleated red blood cells which did not express HLA-ABC, and the intensity of the expression was consistently high; in lymphohematopoietic tumors, the HLA-ABC loss rate was 0.12% (1/869).

Exploration was started in 2008 for the present invention, and a definitive protocol was established in October 2020. 192 patients have been assayed so far, with 130 positive and 62 negative cases, and it was found that screening/diagnosis and follow-up of non-hematopoietic tumors by using the present invention had a coverage and specificity of 99% or more and a sensitivity of 0.01%. The false-positive and false-negative rates were <1%. The non-hematopoietic tumors covered by the present invention refer to the vast majority of types of solid tumors other than lymphohematopoietic tumors published by the World Health Organization, including: tumors of malignant epithelial origin (such as lung cancer, breast cancer, gallbladder cancer, colon cancer, prostate cancer, esophageal cancer, fallopian tube cancer, head and neck cancer, hepatoblastoma, pancreatoblastoma, pancreatic cancer, etc.), embryonal tumors (neuroblastoma, retinoblastoma, germ cell tumor, medulloblastoma, primitive neuroectodermal tumor (PNET), etc.), soft tissue tumors and extraosseous sarcoma (Ewing sarcoma, rhabdomyosarcoma, etc.), bone tumors and cartilage tumors (osteosarcoma, soft tissue sarcoma, etc.), malignant kidney tumors (nephroblastoma, adrenal carcinoma, renal clear cell carcinoma, etc.), malignant melanoma and the like. Above all, with regard to the general field of clinical diagnosis of tumors by flow cytometry, the present invention provides an important protocol of detection and analysis that has a high coverage, great practicality, high sensitivity and high specificity, and can reduce the rate of missed diagnosis.

What is claimed is:

1. A method for detecting a non-hematopoietic tumor by flow cytometry, the method comprising:
   STEP I: preparing a flow cytometry loading sample for detection of the non-hematopoietic tumor by processing a cell sample using a reagent composition,
      wherein the reagent composition comprises a first set of antibodies, a second set of antibodies, and a third set of antibodies, wherein the antibodies in each set are fluorescently-labeled monoclonal antibodies; wherein,
      the first set of antibodies consists of: an anti-CD9 antibody labeled with FITC, an anti-disialoganglioside 2 (GD2) antibody labeled with PE, an anti-CD3 antibody labeled with PerCP-Cy5.5, an anti-CD4 antibody labeled with PE-Cy7, an anti-CD56 antibody labeled with APC, an anti-CD36 antibody labeled with APC-Cy7, an anti-CD81 antibody labeled with BV421, and an anti-CD45 antibody labeled with V500; and the first set of antibodies is to be added to a first flow cytometric tube in which the cell sample to be assayed is in the form of a single cell suspension,
      the second set of antibodies consists of: an anti-human leukocyte antigen (HLA)-ABC antibody labeled with PE, an anti-CD38 antibody labeled with PerCP-Cy5.5, an anti-CD19 antibody labeled with PE-Cy7, an anti-CD56 antibody labeled with APC, an anti-CD36 antibody labeled with APC-Cy7, an anti-CD7 antibody labeled with BV421, and an anti-CD45 antibody labeled with V500; and the second set of antibodies is to be added to a second flow cytometric tube in which the cell sample to be assayed is in the form of a single cell suspension,
      the third set of antibodies consists of: anti-cytoplasmic cytokeratin antibodies labeled with FITC; and the third set of antibodies is to be added to the second flow cytometric tube in which the second set of antibodies has been added and cell sample permeabilization has been performed;
   wherein preparing the flow cytometry loading sample for detection of the non-hematopoietic tumor comprises the steps of:
      (1) adding the cell sample to be assayed into two flow cytometric tubes, the first flow cytometric tube and the second flow cytometric tube, respectively, to form a single cell suspension in each tube and ensure a cell amount of $1 \times 10^6$ cells/tube to $1 \times 10^7$ cells/tube; wherein the cell sample to be assayed is bone marrow, peripheral blood or a tissue cell sample that can be prepared as single live cells suitable for flow cytometry assay;
      (2) adding to the first flow cytometric tube obtained from step (1) the first set of antibodies in the reagent composition, adding to the second flow cytometric tube obtained from step (1) the second set of antibodies in the reagent composition, and incubating each flow cytometric tube at room temperature in the dark;
      (3) adding a solution of a permeabilization reagent A to the second flow cytometric tube after the incubation in step (2) under conditions sufficient to permeabilize the cells in the cell sample, and continuing the incubation at room temperature in the dark;
(4) adding 1× hemolysin to the first flow cytometric tube after the incubation in step (2) under conditions sufficient to hemolyse the cells in the cell sample and adding 1× hemolysin to the second flow cytometric tube after the incubation in step (3) under conditions sufficient to hemolyse the cells in the cell sample, and continuing the incubation at room temperature in the dark;
(5) centrifuging each flow cytometric tube after the incubation in step (4) and removing the supernatant;
(6) adding to the second flow cytometric tube after removing the supernatant in step (5) a solution of a permeabilization reagent B under conditions sufficient to permabilize the cells in the cell sample and the third set of antibodies of the reagent composition, and incubating at room temperature in dark; and
(7) adding a phosphate buffered saline (PBS) buffer for washing to the first flow cytometric tube after removing the supernatant in step (5) and to the second flow cytometric tube after the incubation in step (6), respectively, followed by centrifugation, removal of supernatant, and resuspension of cells with a PBS buffer, to obtain the flow cytometry loading sample; and STEP II: performing a flow cytometry assay, wherein, in the flow cytometry assay:
(i) the gates for the first flow cytometric tube are set as follows: an adherent cell removal gate P1 is set, and a live cell gate P2 is set within P1 to obtain single live cells; blood cells are each gated within the gate P2 with CD45/SSC antibodies; within the gate P2, a gate NH1 is set with CD45/CD56 antibodies to detect CD45$^-$/CD56$^+$ cells, and a gate NH2 is set with CD45/GD2antibodies to detect CD45$^-$/GD2$^+$ cells; within the gate P2, a gate NH3 is set with CD45/CD36 antibodies to detect CD45$^-$/CD36$^+$ cells; the expressions of CD3/CD4/CD36/CD9/CD81 in the cells within the gates NH1 and NH2 are displayed; and the expressions of CD9/GD2/CD56/CD81 in the cells within the gate NH3 are displayed; and ii) the gates for the second flow cytometric tube are set as follows: an adherent cell removal gate P1 is set, and a live cell gate P2 is set within P1 to obtain single live cells; blood cells are each gated within the gate P2 with CD45/SSC antibodies; within the gate P2, a gate NH4 is set with CD45/CD56 antibodies to detect CD45$^-$/CD56$^+$ cells, a gate NH5 is set with a CD45/cytoplasmic cytokeratin antibody to detect CD45$^-$/cytokeratin$^+$ cells; within the gate P2, a gate NH6 is set with CD45/CD36 to detect CD45$^-$/CD36$^+$ cells; the expressions of HLA-ABC/CD38/CD19/CD36/CD7 in the cells within the gates NH4 and NH5 are displayed, and the expressions of cytokeratin/HLA-ABC/CD38/CD56 in the cells within the gate NH6 are displayed;

wherein said non-hematopoietic tumor comprises cells of one or more of: a malignant tumor of epithelial origin, an embryonal tumor, a soft tissue tumor, an extraosseous sarcoma, a bone tumor, a cartilage tumor, a malignant kidney tumor, and a malignant melanoma.

2. The method according to claim 1, wherein each antibody is a monoclonal antibody, and wherein the anti-cytoplasmic cytokeratin antibodies are complexes comprising an anti-CK8 monoclonal antibody, an anti-CK18 monoclonal antibody, and an anti-CK19 monoclonal antibody.

3. The method according to claim 1, wherein
the first set of antibodies is a mixture of an anti-CD9 antibody, an anti-GD2antibody, an anti-CD3 antibody, an anti-CD4 antibody, an anti-CD56 antibody, an anti-CD36 antibody, an anti-CD81 antibody, and an anti-CD45 antibody mixed in a volume ratio of 5:5:5:3:2:3:3:3, and
the second set of antibodies is a mixture of an anti-HLA-ABC antibody, an anti-CD38 antibody, an anti-CD19 antibody, an anti-CD56 antibody, an anti-CD36 antibody, an anti-CD7 antibody, and an anti-CD45 antibody mixed in a volume ratio of 5:5:3:2:3:3:3.

4. The method according to claim 1, wherein the detection of the non-hematopoietic tumor comprises screening, diagnosis and/or follow-up detection.

* * * * *